United States Patent [19]

Fong et al.

[11] Patent Number: 4,577,518

[45] Date of Patent: Mar. 25, 1986

[54] GAS SAMPLING DEVICE

[75] Inventors: Wing C. Fong, Scarborough; Albert J. Fournier, Ajax; Bernard B. Gil, Brampton, all of Canada

[73] Assignee: The Government of Canada, Ottawa, Canada

[21] Appl. No.: 688,222

[22] Filed: Jan. 3, 1985

[30] Foreign Application Priority Data

Jan. 9, 1984 [CA] Canada .................................. 444910

[51] Int. Cl.[4] .......................... G01N 1/14; G01N 1/22
[52] U.S. Cl. ................................ 73/864.91; 141/130; 73/863.01; 73/864.24; 73/864.31
[58] Field of Search ........... 73/863.01, 864.24, 864.31, 73/864.91; 141/130; 422/65, 63, 66

[56] References Cited

U.S. PATENT DOCUMENTS

| | | | |
|---|---|---|---|
| 3,213,669 | 10/1965 | Taft et al. | 141/130 X |
| 3,418,084 | 12/1968 | Allington | 141/130 X |
| 3,638,500 | 2/1972 | Wetzel | 73/864.31 X |
| 4,151,931 | 5/1979 | Scherer et al. | 422/65 X |
| 4,160,473 | 7/1979 | Winchell | 73/864.91 X |
| 4,301,116 | 11/1981 | Ida et al. | 422/65 |
| 4,325,909 | 4/1982 | Coulter et al. | 73/864.24 X |
| 4,476,733 | 10/1984 | Chlosta et al. | 73/864.91 X |

FOREIGN PATENT DOCUMENTS 2037427 3/1971 Fed. Rep. of Germany ...... 141/130
1429052 3/1976 United Kingdom ............ 73/864.91

Primary Examiner—Stewart J. Levy
Assistant Examiner—Tom Noland
Attorney, Agent, or Firm—Saul Elbaum; Alan J. Kennedy; Anthony T. Lane

[57] ABSTRACT

The invention provides apparatus for injecting a sample of a fluid into a sealed pouch. The apparatus includes a framework and an injection needle for coupling to a source of the fluid to supply the fluid to the pouch. A drive mechanism is attached to the framework and is coupled to the injection needle for operation to move the needle between a withdrawn position and an engagement position with the needle moving along a first line of travel. A hopper is attached to the framework for containing a plurality of pouches in a stack, and a transport mechanism is attached to the framework and has a shuttle moveable along a second line of travel at right angles to the first line of travel. The shuttle moves pouches one at a time from the hopper to a position in line with the needle to receive the sample from the needle with the needle in the engagement position. The mechanism also includes an ejection means coupled to the framework and operable to push the pouch off the shuttle to make room for another pouch from the hopper and a control means coupled to the drive mechanism, transport mechanism and ejection means to operate the parts of the apparatus in sequence.

3 Claims, 7 Drawing Figures

GAS SAMPLING DEVICE

BACKGROUND OF THE INVENTION

This invention relates to apparatus for collecting samples fluid in a storage pouch for subsequent transport to a laboratory for testing.

In the field of occupational health and environmental monitoring, it is desirable to collect samples of fluids periodically, and particularly environmental air for subsequent analysis. One of the procedures used is an inflatable bag or pressurized container which requires a pump to inflate or fill the device to an increased pressure. Another device involves the use of an evacuated sampling device to passively fill in response to release of the vacuum into the atmosphere. Such devices suffer from the problem of withdrawal of the sample which, in turn, creates a negative pressure in the container and limits the sample volume. Another method of atmospheric sampling is based upon simple displacement of the interior volume of the container in the atmosphere, for instance by removing water or other liquid from a container and allowing the atmospheric air to enter the container, drawn in by displacement of the liquid. This has the problem of simply organizing the arrangement but also there is the possibility that chemicals in the atmosphere may interact with the liquid.

Another approach is to provide a pouch made up of two layers of MYLAR (trade mark) heat sealed about their peripheries and containing between them a collapsed sponge. Upon piercing one of the layers with an injection needle to feed the sample into the pouch, the sponge tends to separate the layers of mylar and the sample fills the pouch. Once the sample is contained in the pouch, the pouch can be mailed or otherwise transported to a laboratory for subsequent analysis of the sample.

In all of the sampling techniques, including the use of a pouch, it is necessary to have a technician or some other trained person to place the sample in the container. This is an expensive procedure because it is often desirable to take samples on a periodic basis and this means that a technician must be present continuously although his actual work may occupy only a fraction of the technician's time.

Accordingly it is an object of the present invention to automate the collection of samples by prviding apparatus which will place samples periodically in pouches so that the apparatus can be left for a considerable length of time without it requiring a continuous monitoring by a trained technician.

SUMMARY OF THE INVENTION

In one of its aspects, the invention provides apparatus for injecting a sample of a fluid into a sealed pouch. The apparatus includes a framework and an injection needle for coupling to a source of the fluid to supply the fluid to the pouch. A drive mechanism is attached to the framework and is coupled to the injection needle for operation to move the needle between a withdrawn position and an engagement position with the needle moving along a first line of travel. A hopper is attached to the framework for containing a plurality of pouches in a stack, and a transport mechanism is attached to the framework and has a shuttle moveable along a second line of travel at right angles to the first line of travel. The shuttle moves pouches one at a time from the hopper to a position in line with the needle to receive the sample from the needle with the needle in the engagement position. The mechanism also includes an ejection means coupled to the framework and operable to push the pouch off the shuttle to make room for another pouch from the hopper and a control means coupled to the drive mechanism, transport mechanism and ejection means to operate the parts of the apparatus in sequence.

BRIEF DESCRIPTION OF THE DRAWING

This and other aspects of the invention will become apparent from the following description taken in combination with the drawings, in which.

DESCRIPTION OF THE PREFERRED EMBODIMENT

Figure 1:
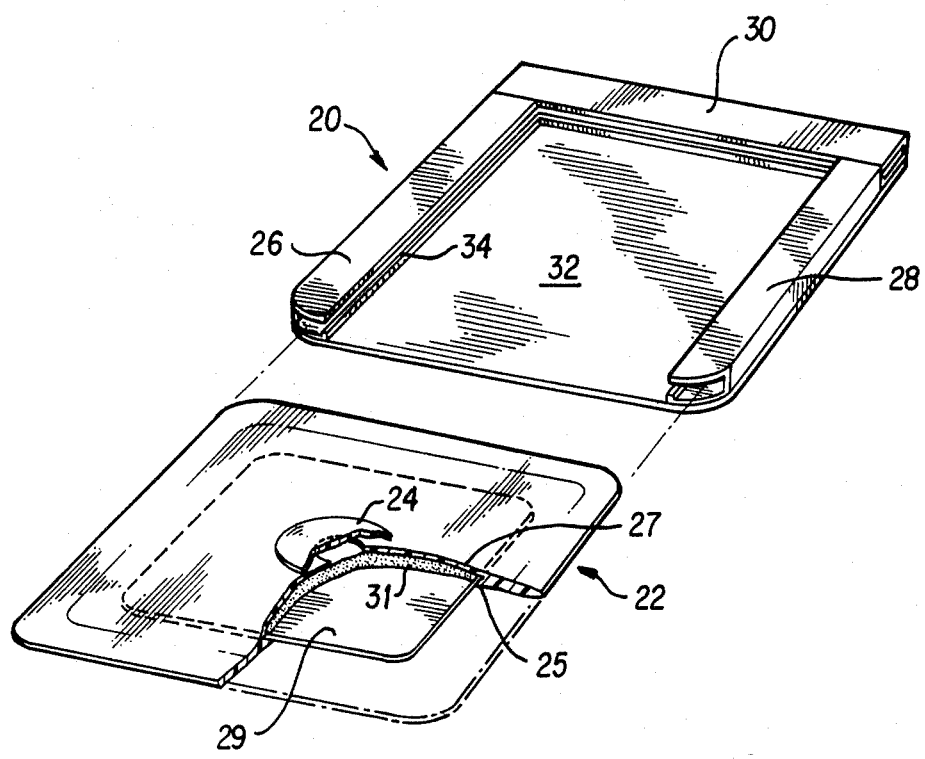
FIG. 1 is an exploded perspective view of a carrier and a pouch, the carrier being adapted to support the pouch for recieving samples of fluid such as air.

Reference is made first to FIG. 1 which illustrates a carrier 20 for supporting a pouch 22 which receives a sample of fluid, usually gas, and more commonly ambient air, through a self-sealing silicone septum 24 which is capable of receiving an injection needle and then sealing itself after withdrawl of the needle. The carrier 20 is designed to receive the pouch and to cooperate with the rest of the apparatus shown in FIG. 2 to transport the pouch into position to receive a sample of fluid and then to reject the pouch and carrier from the apparatus.

The pouch preferably consists of two filmic pieces of MYLAR 25, 27 heat sealed at the edges about a plate 29 of stainless steel foil and containing a sponge 31. The septum 24 is glued to the piece 27 which preferably has an opening covered by the septum as shown.

The carrier 20 consists of two side members 26, 28, a rear member 30 and a base 32 to which the side and rear members are attached. These members are cut from an extrusion which is tubular and generally rectangular in section but which includes a longitudinal slot such as slot 34 in member 26. These slots permit the pouch to be slid into the slots in members 26 and 28 and then into a similar slot in member 30 to thereby control the position of the pouch as the carrier moves through the apparatus as will be described.

Figure 2:
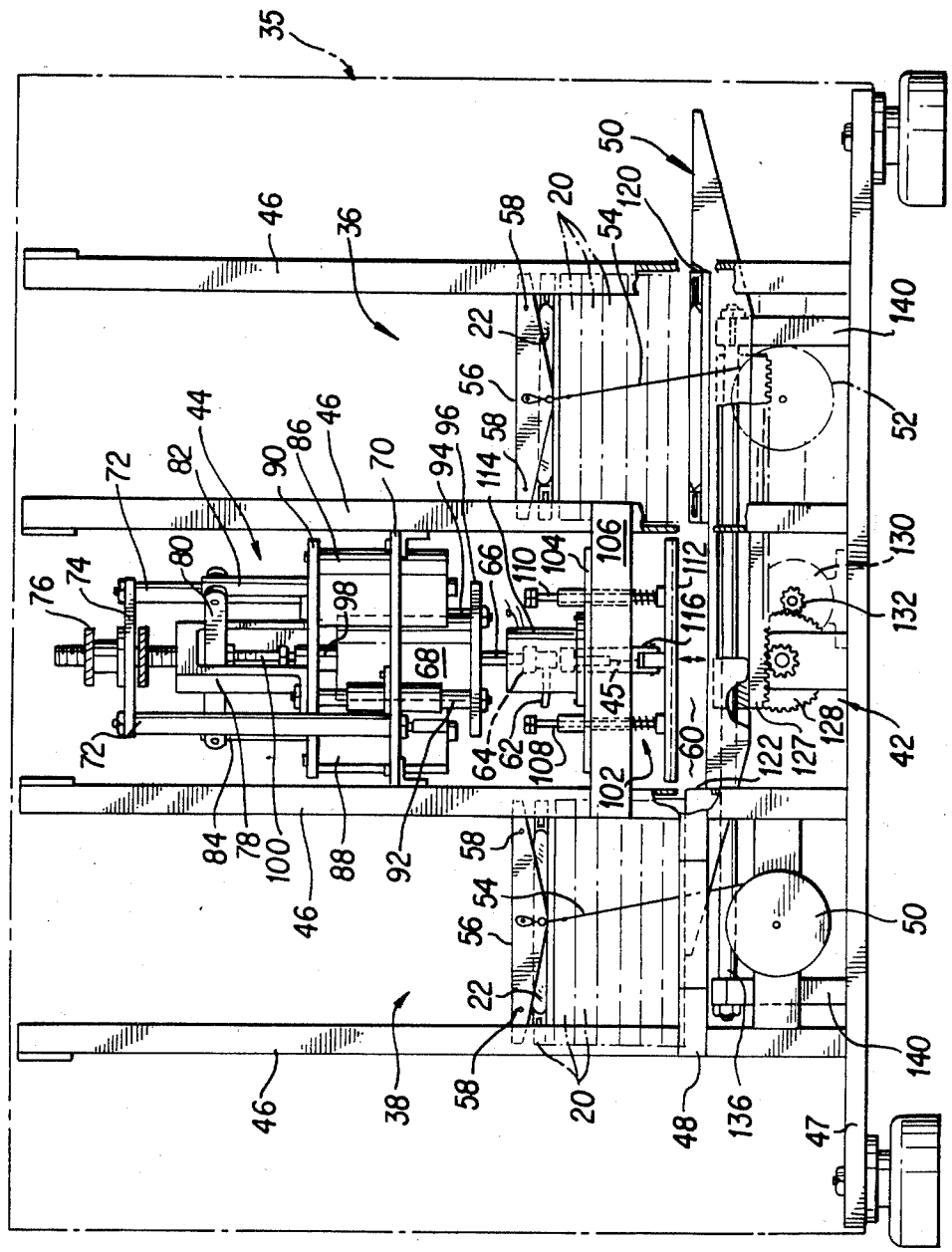
FIG. 2 is a side view with portions broken away and illustrating apparatus for periodically injecting samples into pouches.

Turning now to FIG. 2, apparatus designated generally by the numeral 35 is a preferred embodiment for injecting samples of fluid into pouches on a periodic basis automatically. The apparatus includes a framework carrying a pair of hoppers 36, 38 each of which contains a plurality of carriers 20 having within them pouches 22. Below the hoppers is a transport mechanism 42 which is operational to receive carriers and pouches from the hoppers 36 and 38 alternately and to move individual carriers to a central location under a drive mechanism 44 which carries at its lower end an injection needle 45 for injecting samples, one into each of the pouches. After injection the individual carrier and pouch is ejected from the central location and the transport mechanism picks up a further carrier from one of the hoppers 36, 38 and moves it to the central location to receive the next sample.

Figure 3:
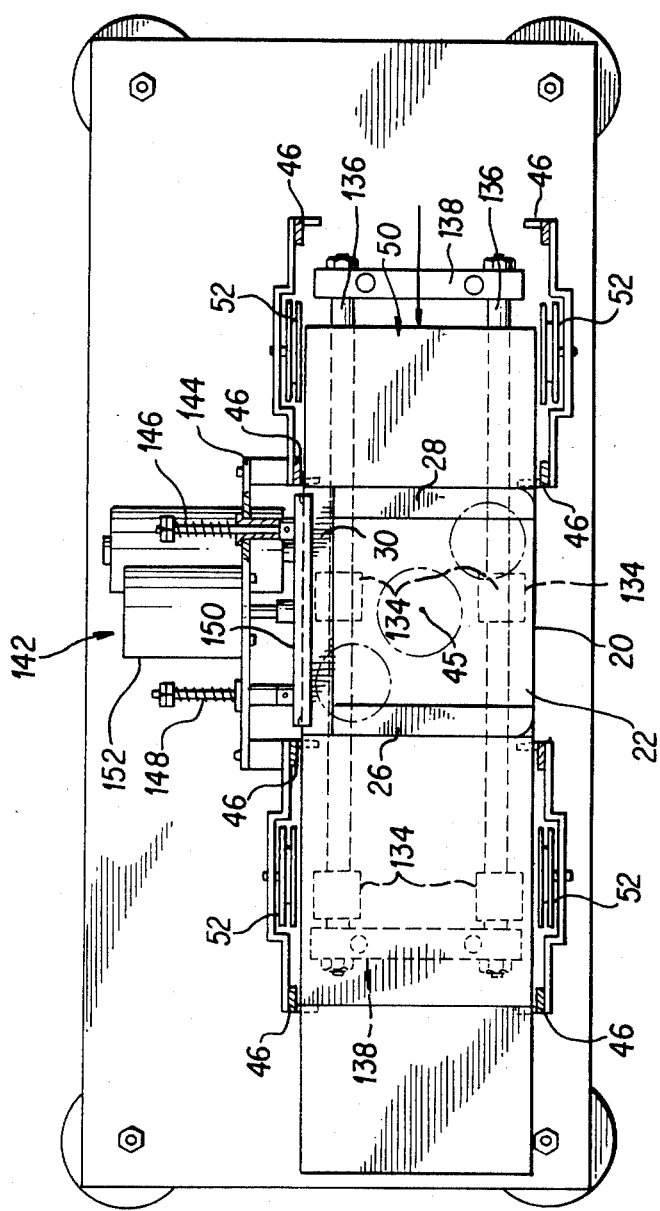
FIG. 3 is a top view of the apparatus also with portions broken away.

Reference is next made to FIGS. 2 and 3 with particular reference to FIG. 2 to describe the apparatus in more detail. The hoppers 36 and 38 are similar and hopper 36 will be described as typical of both of them. The carriers 26 are located between uprights 46 extending from a base 47 and tied together by horizontal members 48 (one of which can be seen) and, together with their respective pouches, the carriers are biased downwardly into engagement with a shuttle 50 forming part of the transport mechanism 42. This biasing is achieved by use of a pair of spring tensioned pulleys 52 which pull captive cables 54 (one of which is seen) downwardly thereby biasing a draw plate 56 into positive engagement with the uppermost one of the carriers. This plate has pairs of pins 58 at both of its sides, one pair of which being visible in FIG. 2. After all of the carriers have been removed by the shuttle 50 from the hopper 36, the pins 58 rest on the horizontal members 48 ending the travel of the draw plate 56.

The transport mechanism 42 is designed to remove carriers and pouches from the hoppers 36, 38 alternately. Each pouch in its carrier is then positioned centrally in the space 60 under the drive mechanism 44 to receive a sample from the needle 45 which is fed through an inlet pipe 62 attached to a coupling 64 which connects the needle to the distal end of a movable rod 66 of a first solenoid actuator 68.

The drive mechanism 44 is supported on an element 70 between inner pairs of uprights 46 and includes a pair of pillars 72 extending upwardly from the element 70. These pillars terminate at a cross-piece 74 which in turn carries an adjuster 76 associated with the upper end of a U-shaped yoke 78. This yoke provides clearance for a straight yoke 80 which links together rods 82, 84 of a pair of solenoid actuators 86, 88 the bodies of which are attached to a plate 90 which in turn is suspended from the lower ends of the U-shaped yoke 78 so that the height of the plate 90 and hence the actuators 86, 88 is adjustable via the adjuster 76 working on the fixed cross-piece 74. Also, the actuator 68 is maintained in fixed relation to the pair of actuators 86, 88 by posts 92, 94 which are attached at their upper ends to the plate 90 and used to hold the yoke 78 in place. The posts 92, 94 are attached at their lower ends to a carrier plate 96 through which the rod 66 projects at its lower end. At the upper end of the actuator 68, an extension 98 of the movable rod projects upwardly terminating in an adjustor 100 which is connected centrally to the straight yoke 80. As a result, any motion of the rod 60 is transmitted to the rods 82, 84 and vice versa.

In operation, the drive mechanism 44 responds to electrical power supplied to the actuators 68, 86 and 88 sequentially. Assuming that the needle 45 is in the withdrawn position as shown in FIG. 2, then upon energizing actuator 68, the needle is driven downwardly into an engagement position shown in FIG. 4. At this point an internal stop in the actuator prevents further downward movement with the plate 29 (FIG. 1) acting as a safety stop. This movement is transmitted also via the yoke 80 to the actuators, 86, 88 thereby moving the pistons in these actuators downwardly. After the sample has passed through the tube 62 and needle 45 into the pouch, power is disconnected from the actuator 68 and applied to the actuators 86, 88 which, through yoke 80, transmit force to the extension 98 of the actuator 68 to move the rod of this actuator upwardly and hence to move the needle out of the pouch. The drive mechanism is then ready to move through a new cycle beginning with removing the electrical power from the actuators 86, 88 and applying it to the actuator 68.

When one of the carriers 20 is positioned in space 60 below the drive mechanism 44, it is held in place by a location device 102. This device is mounted to one side of the needle 45 (i.e. towards the viewer as drawn in FIG. 2) for location on the outer ends of the side members 26, 28 (FIG. 1) of the carriers 20. The device 102 consists of a support member 104 carrying a fixed plate 106 extending horizontally towards the needle 45 and in which are mounted two spring return devices 108, 110 which bias a pressure bar 112 downwardly for engagement with the carrier. The bar 112 can be withdrawn upwardly by a solenoid 114 mounted on the plate 106 and having a coupling 116 attached to the plate 112 which is held in an upward or withdrawn position by the solenoid. Upon release by this solenoid, the devices 108, 110 apply a pre-determined load to the carrier to hold it in position while the needle 45 injects a sample into the pouch contained in the carrier.

Figure 5:
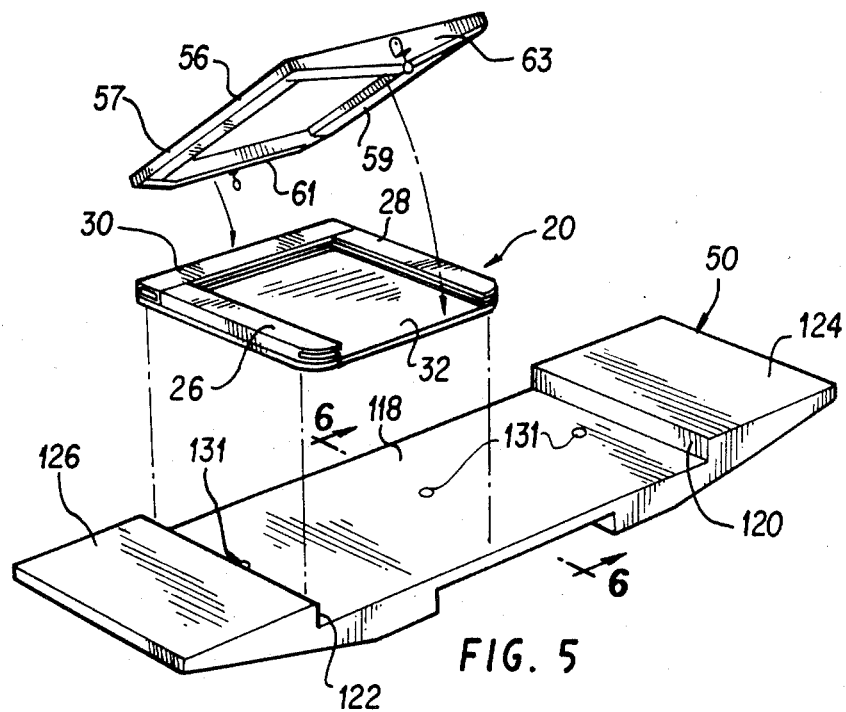
FIG. 5 is a perspective view of a shuttle forming part of a transport mechanism used in the apparatus together with one of the carriers and a draw plate used to move pouches in a hopper towards the shuttle.

As previously described, the shuttle 50 moves between the position shown in FIG. 2 where it receives a carrier from hopper 36 and a corresponding position to the left of the apparatus where it receives a carrier from hopper 38. Turning briefly to FIG. 5, it will be seen that the shuttle has a central recess 118 defined at its ends by parallel shoulders 120, 122. The distance between the shoulders 120, 122 is equal to twice the corresponding width of a carrier so that as seen in FIG. 2, when a new carrier is being picked up from the hopper 36, the shoulder 122 is generally aligned with the end of the pressure bar 112. As also seen in FIG. 5, the shuttle 50 includes a pair of lands 124, 126 outboard from the shoulders 120, 122 and which (as seen in FIG. 2) respectively underlie the hoppers 36, 38 when the other hopper is supplying a pouch. For instance in the FIG. 2 position, the shuttle is receiving a carrier from hopper 36, and the land 126 at the other end of the shuttle is supporting the column of carriers in hopper 38. Consequently there is only one carrier between the shoulders 120, 122 at any given time.

It will be appreciated that when the shuttle picks up a pouch and carrier, it can slide these parts sideways because this carrier slides away from the carrier above it. As the moving carrier leaves, its place is taken effectively by an adjacent one of the lands 124, 126. However there will come a time when the last carrier is leaving from a hopper and this has to slide away from the draw plate, (such as plate 56). As seen in FIG. 5, this plate is effectively a covered frame of two sides 57, 59 a somewhat thicker first end 61 which is bevelled at its ends to blend into sides 57, 59 and a ramped second end 63. The latter end is sufficiently thick that its central part rests on the base 32 of the carrier 20 (with the pouch inside the carrier and inwardly of the end 63)

when the end 61 rests on the rear member 30 of the carrier. In this position the top of the draw plate is horizontal and the pouch is trapped in the carrier. When the last carrier leaves, the ramped end 63 rides over the member 26 while the rear member 30 slides out from under the end 61. The draw plate will then have to ride over the shoulder 120 as the shuttle moves (as will be described) and the ramped end ensures that this will take place without preventing the shuttle moving normally.

Figure 6:
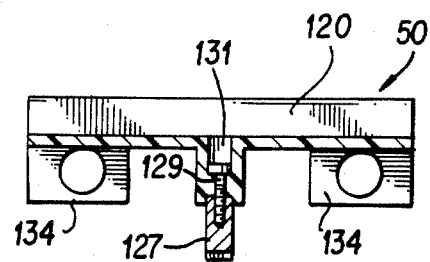
FIG. 6 is a sectional end view generally on line 6—6 of FIG. 5 but showing the shuttle assembled as part of the transport mechanism.

In operation from the position shown in FIG. 2, the shuttle, having received a carrier and pouch from the hopper 36, is made to move to the left by a rack 127 and pinion 128. The rack is attached to the underside of the shuttle by three screws 129 (one of which is shown in FIG. 6). The screws pass through openings 131 in the shuttle (FIGS. 5 and 6).

The pinion 128 is driven by a suitable motor 130 through a pinion and wheel 132. As better seen in FIG. 3, the shuttle includes in its underside four mounting blocks 134 which are bored to ride on a pair of parallel guide rods 136 attached to the framework by posts 140. The rods are separated at their ends by a pair of spacers 138 which act also as stops to locate the shuttle horizontally relative to the hoppers.

Once the injection has taken place, the carrier and pouch are ejected from the apparatus by a kicker mechanism 142 shown in FIG. 3. The kicker mechanism 142 is located on the opposite side of the apparatus from the location device 102 and is designed to eject the carrier and pouch by pushing on the rear member 30. The kicker mechanism 142 is similar in design to the location device and includes a support plate 144 which is attached rigidly to the framework and supports a pair of spring return devices 146, 148 which bias a pressure bar inwardly towards a stored position. A solenoid 152 is operable to eject the carrier and pouch after which the spring return mechanisms return the device to the position shown in FIG. 3.

Figure 4:
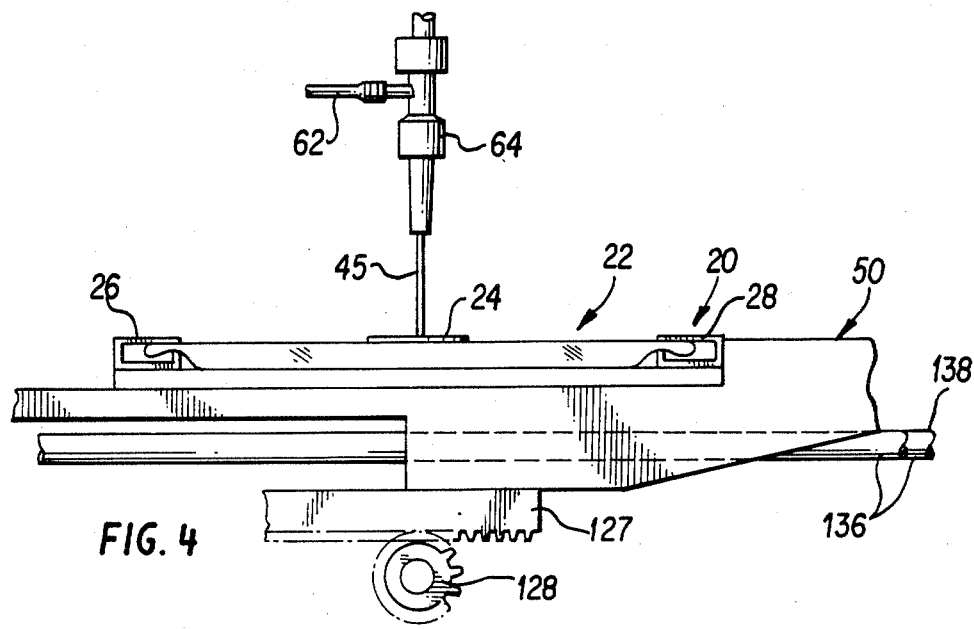
FIG. 4 is a side view (drawn to a larger scale) of a portion of the apparatus shown in FIG. 2 and illustrating a needle engaged in one of the pouches.

In use, the shuttle 50 is driven horizontally by the motor 30 which incorporates a slipping clutch so that the shuttle can be driven into positive engagement with the spacers to locate the shuttle at the ends of its travel. Consequently, after receiving the carrier in the position shown in FIG. 2, the motor is energized to drive the shuttle 50 to the left as drawn until it meets the spacer bar where it stops and the motor then stops. The carrier is now underneath the pressure bar 112 and when the solenoid 114 is de-energized, the spring return devices 108, 110 of the location device 102 push the pressure bar 112 into engagement with the carrier to hold it in place. Next, the drive mechanism 44 is energized as previously described to inject a sample of fluid through the needle 45 into the pouch with the needle in an engagement position as shown in FIG. 4. After withdrawing the needle, the pressure bar 112 is lifted by actuation of the solenoid 114 and the kicker solenoid is activated to eject the pouch. Next the shuttle is moved to the left bringing the shuttle into position to receive a carrier from the hopper 38. The process is repeated sequentially to remove carriers and pouches from the hoppers alternately.

Figure 7:
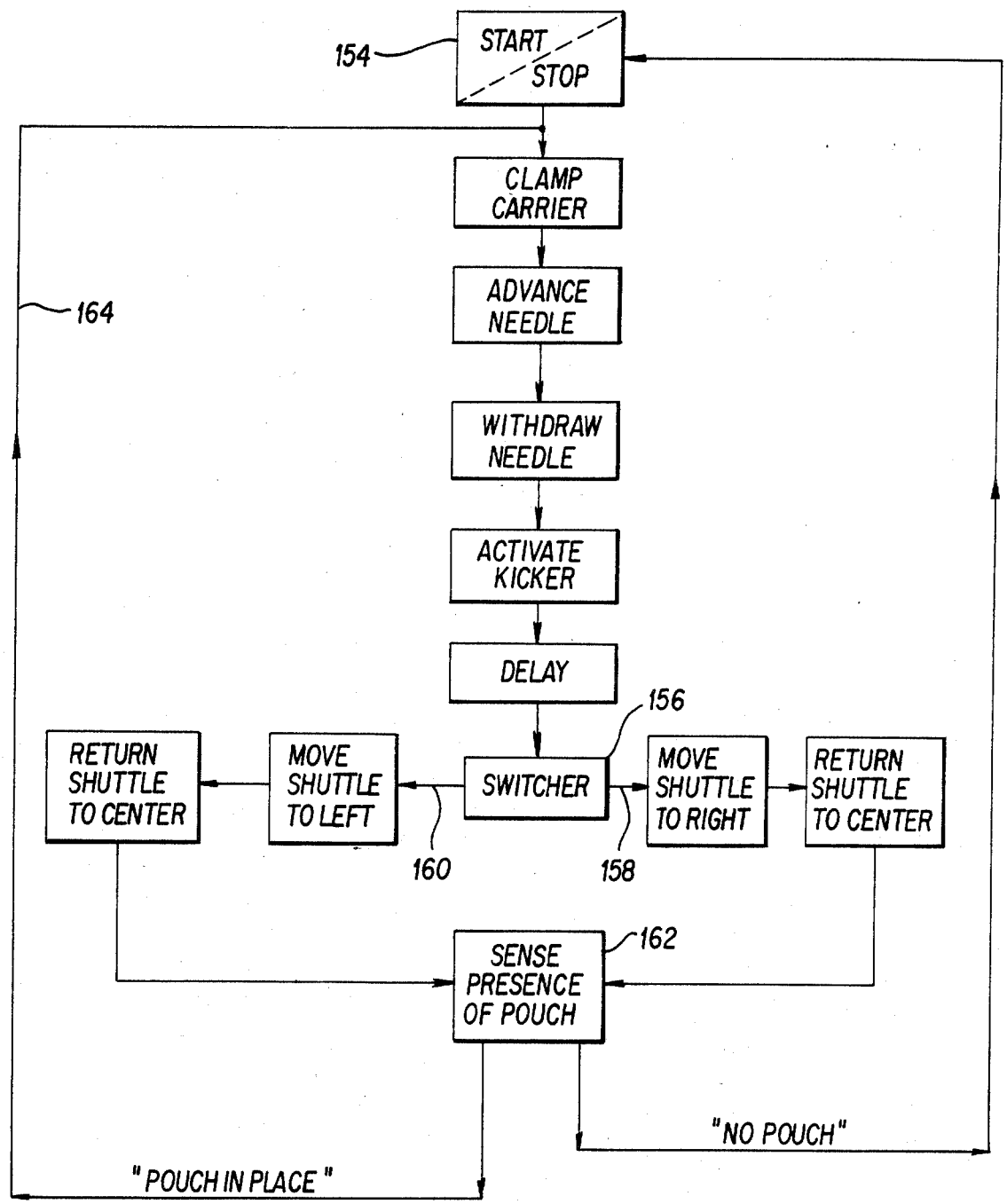
FIG. 7 is a schematic logic diagram showing how the apparatus is controlled to automatically take samples periodically.

The sequence of events will be better understood with reference to the logic diagram FIG. 7. Once the apparatus is activated by energizing the start/stop switch 154, the location device 102 (FIG. 2) is energized to clamp the carrier in place. Next, the needle is advanced by energizing solenoid actuator 68 and, after a suitable delay, the actuators, 86, 88 are energized to withdrawn the needle. Next, the carrier and pouch carrying the sample is removed by the kicker mechanism 142 (FIG. 3) and the apparatus is ready to receive a further sample. However, before this is done, a delay which is built into the control system takes place to space the samples in a predetermined time frame. As also seen in FIG. 7, after the delay, a switcher 156 sends a signal down one of the paths 158, 160. As will be described, the signal is sent alternately and for the moment we assume that the signal goes down path 158. At this point, the shuttle is made to move to the right by the transport mechanism 42 and then, after receiving a carrier and pouch, returns to the center carrying the pouch to receive the sample from the needle. However, before this can take place, a positive response must be received from a sensor 162 and if the sensor shows that a pouch is in place, then a signal is sent along path 164 to cause the carrier to be clamped and the procedure to be repeated. Once the procedure reaches the switcher 156, a signal is sent down path 160 to move the shuttle to the left to receive a pouch and carrier from hopper 38. Again, provided that the sensor 162 shows that a pouch is in place, the procedure will be repeated and of course the next the time the switcher is operated, it will provide a message to path 158. Accordingly, pouches are removed alternately from the hoppers 36 and 38 until no pouches are left at which point the sensor 162 will provide a "no pouch" signal which is fed to the start/stop switch 154 to deactivate the apparatus.

It will be appreciated that the apparatus could be used with a single hopper and a shuttle which moves only between the hopper and the position under the needle. This would demand a hopper of twice the height of that shown for the same number of carriers and it is therefore advantageous to use two hoppers. Modifications of this kind are within the scope of this invention as defined by the claims.

The embodiments of an invention in which an exclusive property or privilege is claimed are defined as follows:

1. Apparatus for injecting samples of a fluid into sealed pouches of a type having a self-sealing portion, the apparatus comprising:
a framework;
an injection needle for coupling to a source of said fluid to supply fluid to the pouches;
a drive mechanism attached to the framework and coupled to the injection needle and operable to move the needle between a withdrawn position and an engagement position along a first line of travel;
a hopper attached to the framework for containing the pouches in a stack;
a transport mechanism attached to the framework and having a shuttle moveable along a second line of travel at right angles to the first line of travel for moving pouches one at a time from the hopper to a position in line with the needle to receive said samples from the needle with the needle in the engagement position;
ejection means coupled to the framework and operable to push the pouches off the shuttle to make space for another one of the pouches from the hopper; and
control means coupled to activate the drive mechanism, transport mechanism, and ejection means sequentially to position the shuttle at the hopper to receive the pouches, to move the shuttle to bring one pouch at a time in line with the needle, to move the needle to the engagement position to provide a sample in this pouch, to move the needle to the withdrawn position, to push the pouch off the shuttle, and to then move the shuttle into position to receive another one of the pouches contained in the hopper before repeating the steps to place a sample in said another one of the pouches.

2. Apparatus for injecting samples of a fluid into sealed pouches of a type having a self-sealing portion, the apparatus comprising:

a framework;

an injection needle for coupling to a source of said fluid to supply fluid to the pouches through the self-sealing portion;

a drive mechanism attached to the framework and coupled to the injection needle and operable to move the needle between a withdrawn position and an engagement position along a first line of travel;

a pair of hoppers attached to the framework, one at each side of said first line of travel, for containing the pouches in two stacks;

a transport mechanism attached to the framework and having a shuttle moveable along a second line of travel at right angles to the first line of travel for moving the pouches one at a time alternately from the hoppers to a position in line with the needle to receive said samples from the needle with the needle in the engagement position;

ejection means coupled to the framework and operable to push the pouches off the shuttle to make space for another one of the pouches from the hoppers; and control means coupled to activate the drive mechanism, transport mechanism, and ejection means sequentially to position the shuttle alternately at the hoppers to receive the pouches, to move the shuttle to bring one pouch at a time in line with the needle, to move the needle to the engagement position to provide a sample in this pouch, to move the needle to the withdrawn position, to push the pouch off the shuttle, and to then move the shuttle into position to receive another one of the pouches contained in the hopper before repeating the steps to place a sample in said another one of the pouches.

3. Apparatus as claimed in claims 1 or 2 and further comprising means biasing the pouches downward into engagement with the shuttle.

* * * * *